US008038993B2

(12) United States Patent
Behrens et al.

(10) Patent No.: US 8,038,993 B2
(45) Date of Patent: Oct. 18, 2011

(54) CYTOTOXIC ANTIBODIES DIRECTED AGAINST ANTIBODIES INHIBITING FACTOR VIII

(75) Inventors: Christian Behrens, Palaiseau (FR); Christine Gaucher, Sequedin (FR); Christophe De Romeuf, Lambersart (FR)

(73) Assignee: LFB Biotechnologies, Les Ulis (FR)

( * ) Notice: Subject to any disclaimer, the term of this patent is extended or adjusted under 35 U.S.C. 154(b) by 84 days.

(21) Appl. No.: 12/084,459

(22) PCT Filed: Nov. 2, 2006

(86) PCT No.: PCT/FR2006/002452
§ 371 (c)(1),
(2), (4) Date: Jul. 25, 2008

(87) PCT Pub. No.: WO2007/051926
PCT Pub. Date: May 10, 2007

(65) Prior Publication Data
US 2009/0130094 A1 May 21, 2009

(30) Foreign Application Priority Data
Nov. 2, 2005 (FR) ..................... 05 11146

(51) Int. Cl.
*A61K 39/395* (2006.01)
(52) U.S. Cl. ............... 424/131.1; 424/133.1; 424/141.1; 424/145.1; 424/146.1; 424/152.1; 435/328
(58) Field of Classification Search .................. None
See application file for complete search history.

(56) References Cited

U.S. PATENT DOCUMENTS

| | | | | |
|---|---|---|---|---|
| 5,693,762 | A * | 12/1997 | Queen et al. | 530/387.3 |
| 7,214,775 | B2 * | 5/2007 | Hanai et al. | 530/387.1 |
| 7,582,296 | B2 * | 9/2009 | Gilles et al. | 424/131.1 |
| 2003/0219861 | A1 * | 11/2003 | Rother et al. | 435/69.1 |
| 2004/0254108 | A1 * | 12/2004 | Ma et al. | 514/12 |
| 2005/0232931 | A1 | 10/2005 | Ma et al. | |
| 2007/0015239 | A1 | 1/2007 | Bihoreau et al. | |
| 2009/0280116 | A1 * | 11/2009 | Smith et al. | 424/133.1 |

FOREIGN PATENT DOCUMENTS

| | | |
|---|---|---|
| EP | 125 023 | 11/1984 |
| FR | 2 861 080 A | 4/2005 |
| WO | WO-01/04269 | 1/2001 |
| WO | WO 02072832 A2 * | 9/2002 |
| WO | WO-2004/014955 A1 | 2/2004 |
| WO | WO-2004/087757 A2 | 10/2004 |
| WO | WO 2006138739 A2 * | 12/2006 |
| WO | WO 2007072866 A1 * | 6/2007 |

OTHER PUBLICATIONS

Portolano et al., J Immunol. Feb. 1, 1993;150(3):880-7.*
Rudikoff et al., Proc Natl Acad Sci U S A. Mar. 1982;79(6):1979-83.*
Janeway et al., Immunobiology, 3rd edition, 1997, Garland Press, pp. 3:1-3:11.*
William E. Paul, M.D., editor, Fundamental Immunology, 3d ed. Raven Press, 1993, p. 242.*
Wood et al., "Expression of active human factor VIII from recombinant DNA clones", Nature, vol. 312, pp. 330-337, (1984).
Gilles, JG et al., "Anti-factor VIII antibodies of hemophiliac patients are frequently directed towards nonfunctional determinants and do not exhibit isotypic restriction", Blood, vol. 82, pp. 2452-2461, (1993).
Jarvis et al., "Induction of Human Factor VIII Inhibitors in Rats by Immunization with Human Recombinant Factor VIII: a Small Animal Model for Humans with High Responder Inhibitor Phenotype", Thromb Haemost., vol. 72(2), pp. 318-325, (1996).
Saint Rémy, JM et al., "Anti-Idiotypic Antibodies: From Regulation to Therapy of Factor VIII Inhibbitors", Vox Sang, 77 (suppl 1), pp. 21-24, (1999).
Morrison et al., "Chimeric human antibody molecules: Mouse antigen-binding domains with human constant region domains", Proc. Natl. Acad. Sci USA, vol. 81, pp. 6851-6855, (1984).
Neuberger et al., "Recombinant antibodies possessing novel effector functions", Nature 312, vol. 5995, pp. 604-608, (1985).
Jacquemin et al., "Mechanism and Kinetics of factor VIII Inactivation: Study With an IgG4 Monoclonal Antibody Derived From a Hemophilia A Patient With Inhibitor", Blood, vol. 92, pp. 496-506, (1998).
Spiegel PC et al., "Structure of a factor VIII C2 domain-immunoglobulin G4κ Fab complex: identification of an inhibitory antibody epitope on the surface of factor VIII", Blood, vol. 98, pp. 13-19, (2001). Almagro, JC et al., "Structural differences between the repertoires of mouse and human germline genes and their evolutionary implications", Immunogenetics, vol. 47, pp. 355-363, (1998).
Lefranc et al., "IMGT unique numbering for immunoglobulin and T cell receptor variable domains and Ig superfamily V-like domains", Dev Comp. Immunmol., vol. 27, pp. 55-57, (2003).
Chothia and Lesk, "Canonical Structures for the Hypervariable Regions of Immunoglobulins", J. Mol. Biol., vol. 196, pp. 901-917, (1987).
Little M. Et. Al: "Of mice and men: hybridoma and recombinant antibodies" Immunology Today, Elsevier Publications, Cambridge, GB, vol. 21, No. 8, Aug. 1, 2000, pp. 364-370.

* cited by examiner

*Primary Examiner* — Michael Szperka
(74) *Attorney, Agent, or Firm* — Birch, Stewart, Kolasch & Birch, LLP

(57) ABSTRACT

The invention relates to an anti-idiotypical antibody targeting an antibody inhibiting the human factor VIII, said inhibiting antibody targeting the C2 region of the human factor VIII, the variable region of each of the light chains thereof being encoded by a sequence of nucleic acids of which at least 70% is identical to the murine sequence of nucleic acids SEQ ID NO: 1, and the variable region of each of the heavy chains thereof being encoded by a sequence of nucleic acids of which at least 70% is identical to the murine sequence of nucleic acids SEQ ID NO: 2, the constant regions of the light chains and the heavy chains being constant regions from a non-murine species. The invention also relates to the use of said antibody for activating the FcγRIII receptors of cytotoxic immune cells, and to the production of a medicament especially for the treatment of haemophilia A.

11 Claims, 5 Drawing Sheets

T0  T16

SEQUENCE LISTING

<160> NUMBER OF SEQ ID NOS: 32

<210> SEQ ID NO 1
<211> LENGTH: 321
<212> TYPE: DNA
<213> ORGANISM: Mus musculus

<400> SEQUENCE: 1

| | | | | | | |
|---|---|---|---|---|---|---|
| gatcttgtgc | taactcagtc | tccagccacc | ctgtctgtga | ctccaggaga | tagtgtcagt | 60 |
| ctttcctgta | gggccagcca | agatattacc | aacacccttc | actggtatca | tcaaaaatca | 120 |
| catgagtctc | caaggcttct | catcaagtat | gtttcccagt | ccatctctgg | atcccctcc | 180 |
| aggttcagtg | gcagtggatc | aggacagtt | ttcactctca | gtatcaacag | tgtgagact | 240 |
| gaagattttg | gagtgtattt | ctgtcagcag | agtaccagct | ggccgtacac | attcggaggg | 300 |
| gggaccaagt | tggaaataaa | a | | | | 321 |

<210> SEQ ID NO 2
<211> LENGTH: 366
<212> TYPE: DNA
<213> ORGANISM: Mus musculus

<400> SEQUENCE: 2

| | | | | | | |
|---|---|---|---|---|---|---|
| gaggtccagc | ttcagcagtc | tggacctgag | ctggttaagc | ctggggcttc | agtgaagctg | 60 |
| tcctgcaagg | cttctggata | cacattcact | agctctgtta | tgcactggct | gaagcagaag | 120 |
| tctgggcagg | gccttgagtg | gattggatat | attaatcctt | acaatgatgg | tactaagtac | 180 |
| aatgagaagt | tcacagccaa | ggccacactg | acttcagaca | atcctccag | cacagtctac | 240 |
| atggagctca | gcggcctgac | ctctgaggac | tttgcggtct | attactgtgc | acgatcggga | 300 |
| ggtttactac | gaggttactg | gtacttcgat | gtctggggcg | cagggaccac | ggtcaccgtc | 360 |
| tcctca | | | | | | 366 |

<210> SEQ ID NO 3
<211> LENGTH: 990
<212> TYPE: DNA
<213> ORGANISM: Homo sapiens

<400> SEQUENCE: 3

| | | | | | | |
|---|---|---|---|---|---|---|
| gcctccacca | agggcccatc | ggtcttcccc | ctggcaccct | cctccaagag | cacctctggg | 60 |
| ggcacagcgg | ccctgggctg | cctggtcaag | gactacttcc | ccgaaccggt | gacggtgtcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacccagacc | 240 |
| tacatctgca | acgtgaatca | caagcccagc | aacaccaagg | tggacaagaa | agttgagccc | 300 |
| aaatcttgtg | acaaaactca | cacatgccca | ccgtgcccag | cacctgaact | cctggggga | 360 |
| ccgtcagtct | tcctcttccc | cccaaaaccc | aaggacaccc | tcatgatctc | ccggacccct | 420 |
| gaggtcacat | gcgtggtggt | ggacgtgagc | cacgaagacc | ctgaggtcaa | gttcaactgg | 480 |
| tacgtggacg | gcgtggaggt | gcataatgcc | aagacaaagc | cgcgggagga | gcagtacaac | 540 |
| agcacgtacc | gtgtggtcag | cgtcctcacc | gtcctgcacc | aggactggct | gaatggcaag | 600 |
| gagtacaagt | gcaaggtctc | caacaaagcc | ctcccagccc | ccatcgagaa | aaccatctcc | 660 |
| aaagccaaag | ggcagcccg | agaaccacag | gtgtacaccc | tgcccccatc | ccgggatgag | 720 |
| ctgaccaaga | accaggtcag | cctgacctgc | ctggtcaaag | gcttctatcc | cagcgacatc | 780 |

-continued

| | |
|---|---|
| gccgtggagt gggagagcaa tgggcagccg agaacaact acaagaccac gcctcccgtg | 840 |
| ctggactccg acggctcctt cttcctctac agcaagctca ccgtggacaa gagcaggtgg | 900 |
| cagcagggga acgtcttctc atgctccgtg atgcatgagg ctctgcacaa ccactacacg | 960 |
| cagaagagcc tctccctgtc tccgggtaaa | 990 |

<210> SEQ ID NO 4
<211> LENGTH: 321
<212> TYPE: DNA
<213> ORGANISM: Homo sapiens

<400> SEQUENCE: 4

| | |
|---|---|
| cggactgtgg ctgcaccaag tgtcttcatc ttcccgccat ctgatgagca gttgaaatct | 60 |
| ggaactgcct ctgttgtgtg cctgctgaat aacttctatc ccagagaggc caaagtacag | 120 |
| tggaaggtgg ataacgccct ccaatcgggt aactcccagg agagtgtcac agagcaggac | 180 |
| agcaaggaca gcacctacag cctcagcagc accctgacgc tgagcaaagc agactacgag | 240 |
| aaacacaaag tctacgcctg cgaagtcacc catcagggcc tgagctcgcc cgtcacaaag | 300 |
| agcttcaaca ggggagagtg t | 321 |

<210> SEQ ID NO 5
<211> LENGTH: 642
<212> TYPE: DNA
<213> ORGANISM: Artificial Sequence
<220> FEATURE:
<223> OTHER INFORMATION: Synthetic Construct

<400> SEQUENCE: 5

| | |
|---|---|
| gatcttgtgc taactcagtc tccagccacc ctgtctgtga ctccaggaga tagtgtcagt | 60 |
| cttcctgtta gggccagcca agatattacc aacacccttc actggtatca tcaaaaatca | 120 |
| catgagtctc caaggcttct catcaagtat gtttcccagt ccatctctgg gatcccctcc | 180 |
| aggttcagtg gcagtggatc agggacagtt ttcactctca gtatcaacag tgtggagact | 240 |
| gaagattttg gagtgtattt ctgtcagcag agtaccagct ggccgtacac attcggaggg | 300 |
| gggaccaagt tggaaataaa acggactgtg gctgcaccaa gtgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag cacccctgacg | 540 |
| ctgagcaaag cagactacga aaacacaaa gtctacgcct gcgaagtcac ccatcagggc | 600 |
| ctgagctcgc ccgtcacaaa gagcttcaac aggggagagt gt | 642 |

<210> SEQ ID NO 6
<211> LENGTH: 1356
<212> TYPE: DNA
<213> ORGANISM: Artificial Sequence
<220> FEATURE:
<223> OTHER INFORMATION: Synthetic Construct

<400> SEQUENCE: 6

| | |
|---|---|
| gaggtccagc ttcagcagtc tggacctgag ctggttaagc ctggggcttc agtgaagctg | 60 |
| tcctgcaagg cttctggata cacattcact agctctgtta tgcactggct gaagcagaag | 120 |
| tctgggcagg gccttgagtg gattggatat attaatcctt acaatgatgg tactaagtac | 180 |
| aatgagaagt tcacagccaa ggccacactg acttcagaca atcctccag cacagtctac | 240 |
| atggagctca gcggcctgac ctctgaggac tttgcggtct attactgtgc acgatcggga | 300 |

| | |
|---|---|
| ggtttactac gaggttactg gtacttcgat gtctggggcg cagggaccac ggtcaccgtc | 360 |
| tcctcagcct ccaccaaggg cccatcggtc ttccccctgg caccctcctc caagagcacc | 420 |
| tctgggggca gcgcggccct gggctgcctg gtcaaggact acttccccga accggtgacg | 480 |
| gtgtcgtgga actcaggcgc cctgaccagc ggcgtgcaca ccttcccggc tgtcctacag | 540 |
| tcctcaggac tctactccct cagcagcgtg gtgaccgtgc cctccagcag cttgggcacc | 600 |
| cagacctaca tctgcaacgt gaatcacaag cccagcaaca ccaaggtgga caagaaagtt | 660 |
| gagcccaaat cttgtgacaa aactcacaca tgcccaccgt gcccagcacc tgaactcctg | 720 |
| gggggaccgt cagtcttcct cttcccccca aaacccaagg acaccctcat gatctcccgg | 780 |
| acccctgagg tcacatgcgt ggtggtggac gtgagccacg aagaccctga ggtcaagttc | 840 |
| aactggtacg tggacggcgt ggaggtgcat aatgccaaga caaagccgcg ggaggagcag | 900 |
| tacaacagca cgtaccgtgt ggtcagcgtc ctcaccgtcc tgcaccagga ctggctgaat | 960 |
| ggcaaggagt acaagtgcaa ggtctccaac aaagccctcc cagcccccat cgagaaaacc | 1020 |
| atctccaaag ccaaagggca gccccgagaa ccacaggtgt acaccctgcc cccatcccgg | 1080 |
| gatgagctga ccaagaacca ggtcagcctg acctgcctgg tcaaaggctt ctatcccagc | 1140 |
| gacatcgccg tggagtggga gagcaatggg cagccggaga caactacaa gaccacgcct | 1200 |
| cccgtgctgg actccgacgg ctccttcttc ctctacagca agctcaccgt ggacaagagc | 1260 |
| aggtggcagc aggggaacgt cttctcatgc tccgtgatgc atgaggctct gcacaaccac | 1320 |
| tacacgcaga agagcctctc cctgtctccg ggtaaa | 1356 |

<210> SEQ ID NO 7
<211> LENGTH: 214
<212> TYPE: PRT
<213> ORGANISM: Artificial Sequence
<220> FEATURE:
<223> OTHER INFORMATION: Synthetic Construct

<400> SEQUENCE: 7

```
Asp Leu Val Leu Thr Gln Ser Pro Ala Thr Leu Ser Val Thr Pro Gly
1               5                   10                  15

Asp Ser Val Ser Leu Ser Cys Arg Ala Ser Gln Asp Ile Thr Asn Thr
            20                  25                  30

Leu His Trp Tyr His Gln Lys Ser His Glu Ser Pro Arg Leu Leu Ile
        35                  40                  45

Lys Tyr Val Ser Gln Ser Ile Ser Gly Ile Pro Ser Arg Phe Ser Gly
    50                  55                  60

Ser Gly Ser Gly Thr Val Phe Thr Leu Ser Ile Asn Ser Val Glu Thr
65                  70                  75                  80

Glu Asp Phe Gly Val Tyr Phe Cys Gln Gln Ser Thr Ser Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                        180                 185                 190
Ala Cys Glu Val Thr His Gln Gly Leu Ser Ser Pro Val Thr Lys Ser
        195                 200                 205

Phe Asn Arg Gly Glu Cys
        210

<210> SEQ ID NO 8
<211> LENGTH: 452
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Ser Ser
            20                  25                  30

Val Met His Trp Leu Lys Gln Lys Ser Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Thr Ala Lys Ala Thr Leu Thr Ser Asp Lys Ser Ser Ser Thr Val Tyr
65                  70                  75                  80

Met Glu Leu Ser Gly Leu Thr Ser Glu Asp Phe Ala Val Tyr Tyr Cys
                85                  90                  95

Ala Arg Ser Gly Gly Leu Leu Arg Gly Tyr Trp Tyr Phe Asp Val Trp
            100                 105                 110

Gly Ala Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335
```

```
Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
        450

<210> SEQ ID NO 9
<211> LENGTH: 107
<212> TYPE: PRT
<213> ORGANISM: Mus musculus

<400> SEQUENCE: 9

Asp Leu Val Leu Thr Gln Ser Pro Ala Thr Leu Ser Val Thr Pro Gly
1               5                   10                  15

Asp Ser Val Ser Leu Ser Cys Arg Ala Ser Gln Asp Ile Thr Asn Thr
            20                  25                  30

Leu His Trp Tyr His Gln Lys Ser His Glu Ser Pro Arg Leu Leu Ile
        35                  40                  45

Lys Tyr Val Ser Gln Ser Ile Ser Gly Ile Pro Ser Arg Phe Ser Gly
    50                  55                  60

Ser Gly Ser Gly Thr Val Phe Thr Leu Ser Ile Asn Ser Val Glu Thr
65                  70                  75                  80

Glu Asp Phe Gly Val Tyr Phe Cys Gln Gln Ser Thr Ser Trp Pro Tyr
                85                  90                  95

Thr Phe Gly Gly Gly Thr Lys Leu Glu Ile Lys
            100                 105

<210> SEQ ID NO 10
<211> LENGTH: 122
<212> TYPE: PRT
<213> ORGANISM: Mus musculus

<400> SEQUENCE: 10

Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Ser Ser
            20                  25                  30

Val Met His Trp Leu Lys Gln Lys Ser Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Thr Ala Lys Ala Thr Leu Thr Ser Asp Lys Ser Ser Ser Thr Val Tyr
65                  70                  75                  80

Met Glu Leu Ser Gly Leu Thr Ser Glu Asp Phe Ala Val Tyr Tyr Cys
                85                  90                  95
```

```
Ala Arg Ser Gly Gly Leu Leu Arg Gly Tyr Trp Tyr Phe Asp Val Trp
            100                 105                 110

Gly Ala Gly Thr Thr Val Thr Val Ser Ser
            115                 120
```

<210> SEQ ID NO 11
<211> LENGTH: 330
<212> TYPE: PRT
<213> ORGANISM: Homo sapiens

<400> SEQUENCE: 11

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 12
<211> LENGTH: 107

```
<212> TYPE: PRT
<213> ORGANISM: Homo sapiens

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 11
<212> TYPE: PRT
<213> ORGANISM: Mus musculus

<400> SEQUENCE: 13

Arg Ala Ser Gln Asp Ile Thr Asn Thr Leu His
1               5                   10

<210> SEQ ID NO 14
<211> LENGTH: 7
<212> TYPE: PRT
<213> ORGANISM: Mus musculus

<400> SEQUENCE: 14

Tyr Val Ser Gln Ser Ile Ser
1               5

<210> SEQ ID NO 15
<211> LENGTH: 9
<212> TYPE: PRT
<213> ORGANISM: Mus musculus

<400> SEQUENCE: 15

Gln Gln Ser Thr Ser Trp Pro Tyr Thr
1               5

<210> SEQ ID NO 16
<211> LENGTH: 5
<212> TYPE: PRT
<213> ORGANISM: Mus musculus

<400> SEQUENCE: 16

Ser Ser Val Met His
1               5

<210> SEQ ID NO 17
<211> LENGTH: 17
<212> TYPE: PRT
<213> ORGANISM: Mus musculus

<400> SEQUENCE: 17

Tyr Ile Asn Pro Tyr Asn Asp Gly Thr Lys Tyr Asn Glu Lys Phe Thr
1               5                   10                  15
```

Ala

<210> SEQ ID NO 18
<211> LENGTH: 13
<212> TYPE: PRT
<213> ORGANISM: Mus musculus

<400> SEQUENCE: 18

Ser Gly Gly Leu Leu Arg Gly Tyr Trp Tyr Phe Asp Val
1               5                   10

<210> SEQ ID NO 19
<211> LENGTH: 24
<212> TYPE: DNA
<213> ORGANISM: Mus musculus

<400> SEQUENCE: 19
actgccatca atcttccact tgac                                              24

<210> SEQ ID NO 20
<211> LENGTH: 23
<212> TYPE: DNA
<213> ORGANISM: Mus musculus

<400> SEQUENCE: 20
ctgagggtgt agaggtcaga ctg                                               23

<210> SEQ ID NO 21
<211> LENGTH: 28
<212> TYPE: DNA
<213> ORGANISM: Mus musculus

<400> SEQUENCE: 21
ttgttcaaga agcacacgac tgaggcac                                          28

<210> SEQ ID NO 22
<211> LENGTH: 28
<212> TYPE: DNA
<213> ORGANISM: Mus musculus

<400> SEQUENCE: 22
gagttccagg tcaaggtcac tggctcag                                          28

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
gtatactagt gccgccacca tggttttcac acctcagat                              39

<210> SEQ ID NO 24
<211> LENGTH: 47
<212> TYPE: DNA
<213> ORGANISM: Artificial Sequence
<220> FEATURE:
<223> OTHER INFORMATION: Primer

<400> SEQUENCE: 24
tgaagacact tggtgcagcc acagtccgtt ttatttccaa cttggtc                     47

<210> SEQ ID NO 25

-continued

```
<211> LENGTH: 41
<212> TYPE: DNA
<213> ORGANISM: Artificial Sequence
<220> FEATURE:
<223> OTHER INFORMATION: Primer

<400> SEQUENCE: 25
ctattactag tgccgccacc atggaatgga gttggatatt t          41

<210> SEQ ID NO 26
<211> LENGTH: 43
<212> TYPE: DNA
<213> ORGANISM: Artificial Sequence
<220> FEATURE:
<223> OTHER INFORMATION: Primer

<400> SEQUENCE: 26
gaccgatggg cccttggtgg aggctgagga gacggtgacc gtg        43

<210> SEQ ID NO 27
<211> LENGTH: 6
<212> TYPE: PRT
<213> ORGANISM: Mus musculus

<400> SEQUENCE: 27

Gln Asp Ile Thr Asn Thr
1               5

<210> SEQ ID NO 28
<211> LENGTH: 3
<212> TYPE: PRT
<213> ORGANISM: Mus musculus

<400> SEQUENCE: 28

Tyr Val Ser
1

<210> SEQ ID NO 29
<211> LENGTH: 9
<212> TYPE: PRT
<213> ORGANISM: Mus musculus

<400> SEQUENCE: 29

Gln Gln Ser Thr Ser Trp Pro Tyr Thr
1               5

<210> SEQ ID NO 30
<211> LENGTH: 8
<212> TYPE: PRT
<213> ORGANISM: Mus musculus

<400> SEQUENCE: 30

Gly Tyr Thr Phe Thr Ser Ser Val
1               5

<210> SEQ ID NO 31
<211> LENGTH: 8
<212> TYPE: PRT
<213> ORGANISM: Mus musculus

<400> SEQUENCE: 31

Ile Asn Pro Tyr Asn Asp Gly Thr
1               5

<210> SEQ ID NO 32
<211> LENGTH: 15
```

-continued

```
<212> TYPE: PRT
<213> ORGANISM: Mus musculus

<400> SEQUENCE: 32

Ala Arg Ser Gly Gly Leu Leu Arg Gly Tyr Trp Tyr Phe Asp Val
1               5                   10                  15
```

CYTOTOXIC ANTIBODIES DIRECTED AGAINST ANTIBODIES INHIBITING FACTOR VIII

This Application is the National Phase Under 35 U.S.C. §371 of PCT International Application No. PCT/FR2006/002452 which has an International filing date of Nov. 2, 2006, which claims priority to French Patent Application No. 0511146 filed on Nov. 2, 2005.

The present invention relates to an anti-idiotypic antibody directed against an antibody inhibiting human factor VIII, said inhibiting antibody being directed against the C2 region of the human factor VIII, the variable region of each of the light chains of which is encoded by a sequence of nucleic acids possessing at least 70% identity with the murine nucleic acid sequence SEQ ID NO: 1, the variable region of each of its heavy chains is encoded by a sequence of nucleic acids possessing at least 70% identity with the murine nucleic acid sequence SEQ ID NO: 2, and the constant regions of the light chains and heavy chains of which are constant regions originating from a non-murine species, as well as the use of this antibody for activating the FcγRIII receptors of cytotoxic immune cells, and for producing a medicament, in particular intended for the treatment of haemophilia A.

INTRODUCTION AND PRIOR ART

Haemophilia A is a hereditary disorder linked to an anomaly of the X chromosome, which results in an inability to coagulate blood in those affected. Haemophilia A is the most common of the deficiencies affecting blood coagulation: in France it affects 1 man in 5000, which represents 80% of haemophilia patients. This disease is the result of mutations on the gene of a protein involved in coagulation, factor VIII (FVIII), which determine either a total absence of FVIII in the blood, or a partial deficiency.

The other type of haemophilia, haemophilia B, affects 20% of haemophilia patients; it is caused by a deficiency in another coagulation factor, factor IX.

The current treatment of haemophilia (of type A or B) involves administering the deficient or missing coagulation factor by intravenous route. In France, FVIII intended for the treatment of type A hemophiliacs is available in the form of medicaments derived from blood supplied by the Laboratoire Français du Fractionnement et des Biotechnologies (LFB) or by international pharmaceutical laboratories, as well as in the form of recombinant medicaments originating from genetic engineering. In fact, the DNA coding for FVIII has been isolated and expressed in mammal cells (Wood et al., Nature (1984) 312: 330-337), and its amino acid sequence deduced from the cDNA.

The secreted FVIII is a glycoprotein with a molecular mass of 300 Kda (2332 amino acids) playing a key role in the activation of the intrinsic coagulation pathway. The inactive FVIII is constituted by six domains: A1 (residues 1-372), A2 (residues 373-740), B (residues 741-1648), A3 (residues 1690-2019), C1 (residues 2020-2172), and C2 (residues 2173-2332), from the N-terminal end to the C-terminal end. After secretion, the FVIII interacts with the von Willebrand factor (vWF) which protects it from plasmatic proteases. The FVIII is dissociated from vWF after cleavage by thrombin. This cleavage leads to the elimination of the B domain and to the formation of a heterodimer. It is in this form that the FVIII circulates in the plasma. This heterodimer is constituted by a heavy chain (A1, A2) and a light chain (A3, C1, C2).

When it is perfused into a hemophiliac patient, the FVIII binds to the vWF in the blood circulation of the patient. The activated FVIII acts as cofactor of the activated factor IX, accelerating the conversion of factor X to activated factor X. The activated factor X converts the prothrombin to thrombin. The thrombin then converts the fibrinogen to fibrin and a clot appears.

The major problem encountered during the administration of FVIII is the appearance in the patient of antibodies directed against FVIII, called "inhibiting antibodies". These antibodies neutralize the procoagulating activity of FVIII, which is rendered inactive as soon as it is perfused. Thus, the coagulation factor administered is destroyed before being able to check hemorrhaging, which constitutes a serious complication of haemophilia, the treatment becoming ineffective. Moreover, certain non-genetically hemophiliac patients can develop inhibitors against endogenous FVIII: it is an acquired haemophilia.

Studies have shown that the anti-FVIII immune response is polyclonal, and mainly directed against the A2 and C2 domains (Gilles J G et al. (1993) Blood; 82: 2452-2461). An animal model was developed in order to study the formation of FVIII inhibitors; rats immunized with recombinant human FVIII exhibit a rapid immune response, of polyclonal type (Jarvis et al. Thromb Haemost. 1996 February; 75 (2):318-25).

The mechanisms by which the anti-FVIII inhibiting antibodies interfere with the function of FVIII are numerous, and include interference in the proteolytic cleavage of FVIII and in the interaction of FVIII with different partners such as vWF, phospholipids (PL), factor IX, activated factor X (FXa) or APC (Activated Protein C).

Several treatments exist making it possible to alleviate the consequences of this immune response, such as for example treatments involving desmopressin which is a synthetic hormone stimulating the production of FVIII, the agents promoting coagulation such as the concentrates of prothrombic complexes or the concentrates of activated prothrombic complexes, the recombinant factor VIIa, plasmapheresis and perfusions of significant or intermediate quantities of FVIII. However, these methods remain very expensive and not very effective.

Another, more recent, strategy envisages the administration of anti-idiotypic antibodies neutralizing the inhibiting antibodies (Saint-Remy J M et al. (1999) Vox Blood; 77 (suppl 1): 21-24). A murine anti-idiotypic monoclonal antibody, 14C12, described in the document WO 2004/014955, neutralizes in vivo in a dose-dependent manner the inhibiting properties of an antibody inhibiting human FVIII. However, these antibodies act only on the neutralization of the antibodies. They have no effect upstream of the secretion of inhibiting antibodies.

Thus a significant need exists for new treatment tools making it possible both to neutralize the circulating inhibiting antibodies and to act upstream of the secretion of the inhibiting antibodies in order to reduce it.

The Applicant has developed a novel tool which is useful in the treatment of haemophilia A possessing both an action on the secreted inhibiting antibodies and an action upstream on the precursors of plasmocytes secreting antibodies inhibiting FVIII, in particular memory B cells.

DESCRIPTION

The Applicant has developed novel cytotoxic anti-idiotypic antibodies, directed against the antibodies inhibiting FVIII, making it possible both to neutralize these circulating inhibiting antibodies by binding to them, and to act on the memory B cells which are at the origin of the plasmocytes which produce these inhibiting antibodies, by causing their lysis by an ADCC (antibody-dependent cell-mediated cytotoxicity) mechanism.

By anti-idiotypic antibody is meant an antibody having the ability to interact with the variable region of other antibodies.

The anti-idiotypic cytotoxic antibody according to the invention is directed against any inhibiting antibody binding to any human FVIII domain, such as the A1 domain, the A2 domain, the B domain, the A3 domain or also the C1 domain. A preferred anti-idiotypic antibody according to the invention is an antibody directed against an inhibiting human antibody binding to the C2 domain of FVIII.

The C2 domain of FVIII contains the phospholipid (PL) binding sites and the major von Willebrand factor (vWF) binding site. The binding of the PLs is essential to the physiological activity of FVIII, in particular for the formation of the tenase complex with factor IX (FIX) and factor X (FX). The vWF acts as a chaperone protein, protecting FVIII against early degradation and clearance. The FVIII-inhibiting antibodies directed against the C2 domain of FVIII are the most frequently encountered inhibitors in patients developing the inhibiting antibodies. Thus, the preferred anti-idiotypic antibodies according to the invention targeting the inhibiting antibodies directed against the C2 domain of FVIII are particularly useful, in that they are capable of affecting a majority of haemophilia A patients having developed inhibiting antibodies.

Thus, an object of the invention relates to an anti-idiotypic monoclonal antibody directed against an antibody inhibiting human FVIII, this inhibiting antibody being directed against the C2 region of human FVIII, the variable region of each of the light chains of the anti-idiotypic monoclonal antibody according to the invention being encoded by a sequence of nucleic acids possessing at least 70% identity with the murine nucleic acid sequence SEQ ID NO: 1, the variable region of each of its heavy chains being encoded by a sequence of nucleic acids possessing at least 70% identity with the murine nucleic acid sequence SEQ ID NO: 2, and the constant regions of its light chains and its heavy chains being constant regions originating from a non-murine species.

Advantageously, the identity of the sequences is at least 70%, preferably at least 80%, and still more preferably at least 95% or at least 99% identity. The percentage identity is calculated by aligning the 2 sequences to be compared and counting the number of positions possessing an identical nucleotide, this number being divided by the total number of nucleotides in the sequence. The degeneration of the genetic code can be at the origin of the fact that the same amino acid can be encoded by several different nucleotide triplets. In any case, these differences in sequences do not affect the specificity of the monoclonal antibody for its target, nor its capacity to neutralize the inhibiting activity of the target inhibiting antibodies by binding to them. Preferentially, the affinity of the antibody according to the invention for its target remains identical or almost identical.

For the purposes of the invention, the equivalent expressions "monoclonal antibody" or "monoclonal antibody composition" refer to a preparation of antibody molecules possessing an identical and unique specificity.

The anti-idiotypic monoclonal antibodies according to the invention, the variable regions of the light chains and the heavy chains of which belong to a species different from the constant regions of the light chains and the heavy chains, is qualified as a "chimeric" antibody.

The anti-idiotypic chimeric antibody according to the invention can be constructed using the standard recombinant DNA techniques, well known to a person skilled in the art, and more particularly using the chimeric antibody construction technique described for example in Morrison et al., Proc. Natl. Acad. Sci. U.S.A., 81: 6851-55 (1984), where the recombinant DNA technology is used in order to replace the constant region of a heavy chain and/or the constant region of a light chain of an antibody originating from a non-human mammal with the corresponding regions of a human immunoglobulin. Such antibodies and their preparation method have also been described in the patent publication EP 173 494, in the document Neuberger, M. S. et al., Nature 312 (5995): 604-8 (1985), as well as in the document EP 125 023 for example.

The murine nucleic acid sequences SEQ ID NO: 1 and SEQ ID NO: 2 encode respectively for the variable domain of each of the light chains and the variable domain of each of the heavy chains of the antibody produced by the murine hybridoma 14C12, available since 30 Jun. 2002 from the Belgian Coordinated Collections of Microorganisms (BCCM), LMBP (plasmid collection, Laboratorium voor Moleculaire Biologie, Universiteit, K. L. Ledeganckstraat 35, 9000 Gent, Belgium), under the accession number LMBP 5878CB. The clone 14C12 has been described in the document WO 2004/014955. The sequences of the murine antibody 14C12 have been chosen to code for the variable regions of the antibody according to the invention or for deriving sequences possessing an identity of at least 70%, advantageously at least 80%, and still more advantageously at least 90% or at least 99%, with these sequences due to the numerous advantageous characteristics of the variable region of the murine antibody 14C12, described in the document WO 2004/014955. A first advantageous aspect of the murine antibody 14C12 is its ability to bind an inhibiting antibody directed against the C2 domain of FVIII, the antibody BO2C11, which is a human monoclonal antibody specific to FVIII derived from the natural repertoire of a patient having developed inhibitors (Jacquemin et al. (1998), *Blood* 92: 496-506) and to inhibit in a dose-dependent manner the binding of this circulating inhibiting antibody to its target, the C2 domain of FVIII. The nucleotide and peptide sequences of the variable regions of the light and heavy chains of the antibody BO2C11 are described in the document WO 01/04269. Moreover, the murine antibody 14C12 has the ability to neutralize in a dose-dependent manner the inhibiting properties of the antibody BO2C11. Moreover, it has been shown that the murine antibody 14C12 neutralizes in vitro 60% of the inhibition of the activity of FVIII observed with antibodies inhibiting polyclonal FVIIIs. The murine antibody 14C12 also significantly neutralizes in vitro the FVIII inhibiting activity observed with polyclonal antibodies originating from a patient different from the patient at the origin of the clone BO2C11, which indicates that the murine antibody 14C12 recognizes an epitope commonly expressed on the human antibodies directed against the C2 domain of FVIII. Concerning the in vivo properties of the murine antibody 14C12, it has been shown in FVIII −/− C57B1/6 mice injected with recombinant human FVIII and the inhibiting antibody BO2C11 that the murine antibody 14C12 neutralizes in a dose-dependent manner the inhibiting properties of the antibody BO2C11, thus confirming the usefulness of the murine antibody 14C12 in therapy for treating patients suffering from haemophilia A having developed inhibitors against the C2 domain of FVIII. Moreover, the murine antibody 14C12 binds with a high affinity to the antibody BO2C11, with $k_{on}$ and $k_{off}$ values of $10^5$ $M^{-1}$ $s^{-1}$ and $10^{-5}$ $s^{-1}$ respectively. Moreover, it has been demonstrated that the variable part of the heavy chain of the murine antibody 14C12 contains both the internal image of the C2 domain made of 13 identical or homologous amino acids, and several contact residues for the variable part of BO2C11. Finally, it has been demonstrated that the murine antibody 14C12 does not inhibit the binding of FVIII to the vWF or to the PL. Thus, the administration of the murine antibody 14C12 to patients suffering from haemophilia A having developed inhibiting antibodies directed against the C2 domain of FVIII does not cause an undesirable inhibition of the functional properties of FVIII. Advantageously, the anti-idiotypic monoclonal antibody according to the invention possesses all the advantageous properties linked to the variable region of the antibody 14C12.

The antibody according to the invention also possesses constant regions of its light and heavy chains belonging to a non-murine species. In this respect, all the families and species of non-murine mammals are capable of being used, and in particular humans, monkeys, the muridae (except for mice), suidae, bovidae, equidae, felidae, canidae, for example, as well as birds, this list not being exhaustive.

Preferably, the variable region of each of the light chains of the anti-idiotypic antibody of the invention is encoded by the murine nucleic acid sequence SEQ ID NO: 1, and the variable region of each of its heavy chains is encoded by the murine nucleic acid sequence SEQ ID NO: 2, the constant regions of its light chains and its heavy chains being constant regions originating from a non-murine species.

Advantageously, the anti-idiotypic monoclonal antibody according to the invention is produced by a cell in the form of an antibody composition, the fucose level/galactose level ratio of the glycan structures of which, present on the glycosylation site of the Fc region of the antibodies, is less than or equal to 0.6. By "glycosylation site of the Fc region", is meant asparagine 297 (Asn 297, Kabat numbering), which carries an N-glycosylation site. In fact, the Fc constant region of the antibodies is constituted by 2 globular domains named CH2 and CH3. The 2 heavy chains interact closely at the level of the C3 domains whereas at the level of the CH2 domains, the presence, on each of the 2 chains, of a biantenna-type N-glycan, bound to the Asn 297, contribute to a separation of the 2 domains. Thus, in the implementation of the invention, the glycan structures carried by all of the glycosylation sites present in the antibody composition show a fucose level/galactose level ratio less than or equal to 0.6, which has been demonstrated in the Patent Application FR 03 12229 to be optimal for conferring a strong ADCC activity ("antibody-dependent cell-mediated cytotoxicity") to the antibodies. The anti-idiotypic antibodies according to the invention therefore have the characteristic and advantage of having an increased ability to activate, by their Fc region, the Fc receptors of cytotoxic effector cells, and in particular the FcγRIIIA receptor (also called CD16), receptor activating cytotoxic effector cells. The effector cells being able to be activated by the anti-idiotypic monoclonal antibody according to the invention are for example NK (Natural Killer) cells, macrophages, neutrophiles, CD8 lymphocytes, Tγδ lymphocytes, NKT cells, eosinophiles, basophiles or mastocytes. Preferably, the anti-idiotypic antibody according to the invention makes it possible to recruit NK cells. The anti-idiotypic monoclonal antibody according to the invention is said to be cytotoxic, and will make it possible to recruit, via its Fc region, effector cells, which will destroy the cell carrying at its surface the target of the anti-idiotypic antibody according to the invention.

Thus, the antibody according to the invention allows the destruction of cells expressing at their surface said FVIII inhibiting antibody, which are the precursors of plasmocytes secreting FVIII inhibiting antibodies, in particular the memory B cells.

Preferably, the target cells are memory B cells.

Thus, the anti-idiotypic monoclonal antibody according to the invention will on the one hand inhibit the binding of FVIII inhibiting antibody by binding to the idiotope of the inhibiting antibody, and on the other hand cause the lysis of the memory B cells expressing at their surface the target inhibiting antibody and precursors of the plasmocytes secreting the inhibiting antibodies, these two effects participating in the reduction of the inhibiting effect of FVIII inhibiting antibodies produced by the hemophiliac patient.

Preferably, the anti-FVIII inhibiting antibody against which the anti-idiotypic antibody of the invention is directed is the antibody BO2C11. This antibody is a human IgG4kappa monoclonal antibody specific to FVIII derived from the natural repertoire of a patient suffering from haemophilia A having inhibitors (Jacquemin M G et al. (1998) Blood 92: 496-506). The antibody BO2C11 recognizes the C2 domain and inhibits the binding of FVIII to the vWF and to the phospholipids (PL), this action mechanism being most commonly encountered in patients having inhibiting antibodies specific to the C2 domain of FVIII. Moreover, the precise binding site of the antibody BO2C11 to the C2 domain has been identified by X-ray analysis of crystals of Fab fragments and of the C2 domain (Spiegel P C et al. (2001) Blood 98:13-19). The amino acid and nucleotide sequences of the variable regions of the heavy chains and the light chains of the antibody BO2C11 have been described in the document WO 01/04269, dating from 2000.

Thus, the anti-idiotypic antibody according to the invention recognizes the circulating antibody BO2C11, as well as the membrane antibody BO2C11 (BCR) situated at the surface of the clone of memory B cell BO2C11. The anti-idiotypic antibody according to the invention will therefore on the one hand neutralize the circulating antibody by binding to it, and on the other hand bind to the membrane immunoglobin, which will be followed by binding between the Fc region of the antibody according to the invention and the cytotoxic cells via the Fc receptor of these cytotoxic cells. The antibody according to the invention will therefore participate in the lysis of the memory B cells expressing the immunoglobulin BO2C11 at their surface.

Preferably, the constant regions of each of the light chains and each of the heavy chains of the anti-idiotypic antibody according to the invention are human constant regions. This preferred embodiment of the invention makes it possible to reduce the immunogenicity of the antibodies in humans and hence even to improve its effectiveness during its therapeutic administration to humans.

In a preferred embodiment of the invention, the constant region of each of the light chains of the antibody according to the invention is of type κ (kappa). Any allotype is suitable for carrying out the invention, for example Km(1), Km(1, 2), Km(1, 2, 3) or Km (3) but the preferred allotype is Km (3).

In another complementary embodiment, the constant region of each of the light chains of the antibody according to the invention is of type λ (lambda).

In a particular aspect of the invention, and in particular when the constant regions of each of the light chains and each of the heavy chains of the antibody according to the invention are human regions, the constant region of each of the heavy chains of the antibodies is of type γ (gamma). According to this variant, the constant region of each of the heavy chains of the antibodies can be of type γ1, γ2, or γ3, these three types of constant regions having the characteristic of binding the human complement, or also of type γ4. The antibodies possessing a constant region of each of the heavy chains of type γ belong to the IgG class. The type G immunoglobulins (IgG), are heterodimers constituted by 2 heavy chains and 2 light chains, linked to each other by disulphide bridges. Each chain is constituted, at the N-terminal position, by a variable region or domain (encoded by the rearranged V-J genes in the case of the light chain and V-D-J in the case of the heavy chain) specific to the antigen against which the antibody is directed, and at the C-terminal position, by a constant region, constituted by a single CL domain in the case of the light chain or 3 domains (CH1, CH2 and CH3) in the case of the heavy chain. The combination of the variable domains and the CH, and CL domains of the heavy and light chains form the Fab regions, which are connected to the Fc region by a very flexible hinge region allowing each Fab to bind to its antigen target whereas the Fc region, which mediates the effector properties of the antibody, remains accessible to the effector molecules such as the receptors FcγR and the C1q. The Fc region, constituted by the 2 globular domains $CH_2$ and $CH_3$, is glycosylated at the level of the domain CH2 with the presence, on each of the 2 chains, of a biantenna-type N-glycan, bound to the Asn 297.

Preferably, the constant region of each of the heavy chains of the antibodies is of type γ1, as such antibodies exhibit an ability to produce an ADCC activity in the largest number of individuals (humans). In this respect, any allotype is suitable for carrying out the invention, for example G1m (3), G1m(1, 2, 17), G1m(1, 17) or G1m(1, 3). Preferably, the allotype is G1m(1, 17).

In a particular aspect of the invention, the constant region of each of the heavy chains of the antibodies is of γ1 type, and it is encoded by a sequence of nucleic acids possessing at least 70% identity with the human nucleic acid sequence SEQ ID NO: 3, the constant region of each of its light chains being encoded by a sequence possessing at least 70% identity with the human nucleic acid sequence SEQ ID NO: 4.

Advantageously, the identity of the sequences mentioned above is at least 80%, and particularly advantageously at least 90% or 99%, the sequence modifications not modifying the functional properties of the antibody according to the invention.

Preferably, the constant region of each of the heavy chains of the antibody according to the invention is of γ1 type and is encoded by the human nucleic acid sequence SEQ ID NO: 3 and the constant region of each of its light chains is encoded by the human nucleic acid sequence SEQ ID NO: 4.

Thus, such an antibody possesses a variable murine region and a constant human region, with heavy chains of γ1 type. This antibody therefore belongs to the human IgG1 sub-class. This antibody possesses two light chains the variable domain of which is encoded by the murine nucleic acid sequence SEQ ID NO: 1 and the constant human region of which is encoded by the nucleic acid sequence SEQ ID NO: 4, and two heavy chains the variable domain of which is encoded by the murine nucleic acid sequence SEQ ID NO: 2 and the constant region of which is encoded by the human nucleic acid sequence SEQ ID NO: 3.

In another aspect of the invention, each of the light chains of the antibody according to the invention is encoded by a sequence possessing at least 70% identity with the murine-human chimeric nucleic acid sequence SEQ ID NO: 5, and each of the heavy chains is encoded by a sequence possessing at least 70% identity with the murine-human chimeric nucleic acid sequence SEQ ID NO: 6. In a particular advantageous manner, the sequence identities are of at least 80%, and still more advantageously of at least 90% or of at least 99%, the sequence modifications modifying neither the specificity of the antibody nor its functional properties.

Preferably, each of the light chains of the antibody according to the invention is encoded by the murine-human chimeric nucleic acid sequence SEQ ID NO: 5, and each of the heavy chains is encoded by the murine-human chimeric nucleic acid sequence SEQ ID NO: 6.

The murine-human chimeric nucleic acid sequence SEQ ID NO: 5 coding for each of the light chains of the antibody is obtained by fusion of the murine nucleic acid sequence SEQ ID NO: 1 coding for the variable domain of each of the light chains of the antibody and of the human nucleic acid sequence SEQ ID NO: 4 coding for the constant region of each of the light chains of the antibody. The murine-human chimeric nucleic acid sequence SEQ ID NO: 6 coding for each of the heavy chains of the antibody is obtained by fusion of the murine nucleic acid sequence SEQ ID NO: 2 coding for the variable domain of each of the heavy chains of the antibody and the human nucleic acid sequence SEQ ID NO: 3 coding for the constant region of each of the heavy chains of the antibody. Advantageously, each of the light chains of the antibody according to the invention possesses a peptide sequence having at least 70% identity with the peptide sequence SEQ ID NO: 7, and each of the heavy chains of the antibody according to the invention possesses a peptide sequence having at least 70% identity with the peptide sequence SEQ ID NO: 8. In particularly advantageous manner, the identity between the sequences is at least 80%, 90%, or also 95%, or 99%, the sequence modifications modifying neither the specificity of the antibody nor its functional properties.

Preferably, the peptide sequence of each of the light chains of the antibody according to the invention is the peptide sequence SEQ ID NO: 7, and the peptide sequence of each of the heavy chains of the antibody according to the invention is the peptide sequence SEQ ID NO: 8.

Thus, when each of the light chains of the antibody is encoded by the murine-human chimeric nucleic acid sequence SEQ ID NO: 5, and each of the heavy chains is encoded by the murine-human chimeric nucleic acid sequence SEQ ID NO: 6, the peptide sequence of each of the light chains, deduced from the nucleic acid sequence SEQ ID NO: 5 is the sequence SEQ ID NO: 7 and the peptide sequence of each of the heavy chains, deduced from the nucleic acid sequence SEQ ID NO: 6, is the sequence SEQ ID NO: 8.

The antibody according to the invention can be produced by any cell line, and more particularly by a cell line producing antibodies having a strong affinity for $CD^{16}$.

In a particularly advantageous manner, the antibody of the invention is produced by a rat myeloma cell line. The line producing the antibody according to the invention is an important characteristic since it confers certain of its particular properties on the antibody. In fact, the means of expression of the antibodies is at the origin of the post-translational modifications, in particular glycosylation modifications, which can vary from one cell line to the other, and thus confer different functional properties to antibodies nevertheless having identical primary structures.

In a preferred embodiment, the antibody is produced in the rat myeloma YB2/0 (cell YB2/3HL.P2.G11.16Ag.20, deposited at the American Type Culture Collection under number ATCC CRL-1662). This line was chosen due to its ability to produce antibodies having an improved ADCC activity relative to antibodies of the same primary structure produced for example in CHO, and to the absence of endogenous immunoglobulin production. Thus, the antibodies according to the invention produced in the cell line YB2/0 have an increased ability to activate, by their Fc region, the Fc receptors of the cytotoxic cells compared with antibodies of the same primary structure produced in another cell line. Moreover, this cell line has the characteristic and advantage of producing antibodies in the form of an antibody composition, the fucose level/galactose level ratio of the glycan structure of which, present on the glycosylation site of the Fc region of the antibodies, is less than or equal to 0.6.

Advantageously, the antibody according to the invention is capable of being produced by the clone R565, deposited on 25 Oct. 2005, under number I-3510 in the Collection Nationale de Culture des Microorganismes (CNCM, 25 rue du Docteur Roux, 75724 Paris cedex 15).

Advantageously, the antibody according to the invention is the antibody EMAB565, produced by the clone R565. Each of the light chains of the antibody EMAB565 is encoded by the murine-human chimeric nucleic acid sequence SEQ ID NO: 5, and each of its heavy chains is encoded by the murine-human chimeric nucleic acid sequence SEQ ID NO: 6. This chimeric antibody enters into competition with the murine antibody 14C12 for binding FVIII and possesses an increased cytotoxic activity, much greater than that of the murine 14C12, which can be partly attributed to the particular glycosylation of the N-glycan of the heavy chain of these antibodies. In fact, the clone R565 has the characteristic of producing a composition of antibody EMAB565 possessing a fucose level/galactose level ratio less than 0.6, for which it has been demonstrated in Patent Application FR 03 12229 that it is optimal for conferring a strong ADCC activity on the antibodies. This antibody is therefore particularly useful as a therapeutic tool for the treatment of pathologies the cells of which to be targeted express FVIII inhibiting antibodies.

The invention also covers any monoclonal antibody possessing substantially the same characteristics as the antibody EMAB565.

Another subject of the invention relates to an expression vector of the light chain of an antibody according to the invention. This vector is the vector allowing the expression of an antibody according to the invention the light chain of which is encoded by the nucleic acid sequence SEQ ID NO: 5, the peptide sequence deduced from which is the sequence SEQ ID NO: 7. This vector is a nucleic acid molecule into which the murine nucleic acid sequence SEQ ID NO: 1 coding for the variable domain of each of the light chains of the antibody and the nucleic acid sequence SEQ ID NO: 4 coding for the constant region of each of the light chains of the antibody have been inserted, in order to introduce them into and maintain them in a host cell. It allows the expression of these foreign nucleic acid fragments in the host cell as it possesses sequences (promoter, polyadenylation sequence, selection gene) indispensable for selection and expression. Such vectors are well known to a person skilled in the art, and can be an adenovirus, a retrovirus, a plasmid or a bacteriophage, this list not being limitative. Moreover, any mammal cell can be used as a host cell, i.e. as a cell expressing the antibody according to the invention, for example YB2/0, CHO, CHO dhfr- (for example CHO DX B11, CHO DG44), CHO Lec 3, SP2/0, NSO, 293, BHK or COS.

Another object of the invention relates to an expression vector of the heavy chain of an antibody according to the invention. This vector is the vector allowing the expression of an antibody according to the invention the heavy chain of which is encoded by the nucleic acid sequence SEQ ID NO: 6, the deduced peptide sequence of which is the sequence SEQ ID NO: 8. This vector is a nucleic acid molecule into which the murine nucleic acid sequence SEQ ID NO: 2 coding for the variable domain of each of the heavy chains of the antibody and the human nucleic acid sequence SEQ ID NO: 3 coding for the constant region of each of the heavy chains of the antibody have been inserted, in order to introduce them into and maintain them in a host cell. It allows the expression of these foreign nucleic acid fragments in the host cell as it possesses sequences (promoter, polyadenylation sequence, selection gene) indispensable to this expression. Just as indicated previously, the vector can be for example a plasmid, an adenovirus, a retrovirus or a bacteriophage, and the host cell can be any mammal cell, for example YB2/0, CHO, CHO dhfr- (CHO DX B11, CHO DG44), CHO Lec13, SP2/0, NSO, 293, BHK or COS.

An antibody produced by co-expression of the expression vectors of the heavy chain and the light chain in the cell YB2/0 is illustrated by the antibody EMAB565, produced by the clone R565 (deposited under registration no. I-3510 in the CNCM). This antibody induces a cytotoxicity much greater than that induced by the murine antibody 14C12 in the presence of human NK cells. Moreover, the antibody EMAB565 induces a much greater secretion of IL-2 (interleukin 2) by Jurkat-CD16 cells than the murine antibody 14C12. The antibody EMAB565, which can be produced by culture of the clone R565 in a culture medium and under conditions allowing the expression of the vectors previously described, is therefore one of the most useful tools capable of advancing the therapy and diagnosis of the pathologies involving BO2C11, and more particularly haemophilia A, as well as research in this field.

Another particular subject of the invention is a stable cell line expressing an antibody according to the invention.

Advantageously, the stable cell line expressing an antibody according to the invention is chosen from the group consisting of: SP2/0, YB2/0, IR983F, a human myeloma such as Namalwa or any other cell of human origin such as PER.C6, the CHO lines, in particular CHO-K-1, CHO-Lec10, CHO-Lec1, CHO-Lec13, CHO Pro-5, CHO dhfr- (CHO DX B11, CHO DG44), or other lines chosen from Wil-2, Jurkat, Vero, Molt-4, COS-7, 293-HEK, BHK, K6H6, NSO, SP2/0-Ag 14 and P3X63Ag8.653. Preferably, the line used is rat myeloma YB2/0. This line has been chosen due its ability to produce antibodies having an improved ADCC activity compared with antibodies of the same primary structure produced for example in CHO.

In a particular aspect of the invention, the stable cell line expressing an antibody according to the invention, and more particularly chosen from the group described previously, has integrated the two expression vectors of the heavy chain and the light chain, as described previously.

A particular aspect of the invention relates to the clone R565 deposited under registration number I-3510 in the Collection Nationale de Cultures de Microorganismes (CNCM).

The present invention also relates to any cell line producing a monoclonal antibody possessing a reactivity substantially similar to that of the antibody EMAB565 produced by the line R565 as described above.

Another particular subject of the invention relates to an anti-idiotypic monoclonal antibody binding to an antibody directed against the C2 domain of human FVIII and produced by the clone R565.

Another object of the invention relates to a DNA fragment of sequence SEQ ID NO: 6 coding for the heavy chain of an antibody according to the invention. The murine-human chimeric nucleic acid sequence SEQ ID NO: 6 codes for each of the heavy chains of the antibody. It is obtained by fusion of the murine nucleic acid sequence SEQ ID NO: 2 coding for the variable region of each of the heavy chains of the antibody and the human nucleic acid sequence SEQ ID NO: 3 coding for the constant region of each of the heavy chains of the antibody.

Another particular object of the invention relates to a DNA fragment of sequence SEQ ID NO: 5 coding for the light chain of an antibody according to the invention. The murine-human chimeric nucleic acid sequence SEQ ID NO: 5 codes for each of the light chains of the antibody. It is obtained by fusion of the murine nucleic acid sequence SEQ ID NO: 1 coding for the variable region of each of the light chains of the antibody and the human nucleic acid sequence SEQ ID NO: 4 coding for the constant region of each of the light chains of the antibody.

Another object of the invention is the use of an, advantageously monoclonal, anti-idiotypic antibody, directed against an inhibiting antibody of human FVIII for the recruitment, in vivo or in vitro, by the Fc region of said anti-idiotypic antibody, of cytotoxic immune cells. Such a use can be implemented with any cytotoxic anti-idiotypic antibody directed against any domain of FVIII. These cytotoxic anti-idiotypic antibodies will activate the FcγRIII receptors, and in particular the FcγRIIIA receptors of cytotoxic immune cells. Advantageously, the antibody used is an antibody according to the invention as described previously, and in a particularly advantageous manner, it is the antibody EMAB565.

The antibodies of the invention have the ability to activate, by their Fc region, the FcγRIIIA receptor. This represents a considerable benefit, as this receptor is expressed at the surface of cells called "effector cells": the binding of the Fc region of the antibody to its receptor carried by the effector cell causes the activation of the FcγRIIIA of the effector cell and the destruction of the target cells. The effector cells are for example NK (Natural Killer) cells, macrophages, neutrophiles, CD8 lymphocytes, Tγδ lymphocytes, NKT cells, eosinophiles, basophiles or mastocytes.

Advantageously, such a use can be carried out for the destruction, in vivo or in vitro, of precursor cells of plasmocytes secreting inhibiting antibodies of FVIII, expressing at their surface an FVIII inhibiting antibody. Preferably, these cells are B cells, in particular memory B cells. Advantageously, this inhibiting antibody is directed against the C2 domain of FVIII.

The B lymphocytes express at their surface a receptor for the antigen (BCR for "B-cell receptor") which is constituted by a membrane immunoglobin associated with other proteins. Each B lymphocyte synthesizes only a single variety of membrane immunoglobin the variable regions of which are identical to those of the secreted antibodies. The B lymphocytes directly recognize the antigens by their BCR. The binding of an antigen by the BCR, if it is accompanied by other essential signals, can trigger the multiplication of said B lymphocyte causing the formation of a clone by multiplication of this lymphocyte. Some of the B lymphocytes originating from the mitoses are differentiated to circulating antibody secreting plasmocytes, the others forming memory B lymphocytes, inactive at the end of this first reaction.

Patients suffering from haemophilia A (in particular severe haemophilia A) have very little or no endogenous FVIII, i.e. this protein is foreign to their organism, and the FVIII administered can trigger an immune reaction during its first administration or a subsequent administration. The binding between the FVIII administered and the BCR expressed on a B lymphocyte, on condition that it has sufficient affinity, can activate the B lymphocyte, resulting in the secretion of soluble anti-FVIII antibodies by plasmocytes and in the formation of memory B lymphocytes expressing at their surface a BCR specific to FVIII. In the case of a new contact with FVIII, these memory B lymphocytes multiply in order to increase the number of memory B lymphocytes with the same specificity and are differentiated to plasmocytes which secrete anti-FVIII antibodies with a high affinity.

The reaction produced by the memory B lymphocytes is more intense than that produced by naive B lymphocytes, these memory cells being more numerous and having a BCR with more affinity than the lymphocytes from which they originated. Moreover, the differentiation to plasmocytes is more rapid from the memory cells than from the initial cells with the same specificity.

The membrane immunoglobin, due to its specificity relative to a certain antigen, is a distinctive characteristic of a B lymphocyte. A B lymphocyte having an anti-FVIII BCR and giving rise to plasmocytes secreting FVIII inhibiting antibodies, can then be targeted by an antibody binding to the portions of the immunoglobulin which give the specificity to the anti-FVIII antibodies. Thus, the antibody according to the invention recognizes the membrane immunoglobin, and, by means of the recruitment of cytotoxic immune cells by its Fc region is responsible for the lysis of the cells expressing the BCR at their surface.

More particularly, such a use can be carried out for the destruction, in vivo or in vitro, of memory B cells expressing at their surface a BCR having the variable regions of the light chains (VL) and the variable regions of the heavy chains (VH) of the antibody BO2C11. This destruction takes place via an antibody-dependent cell elimination mechanism, in particular ADCC.

Another particular subject of the invention is the use of the antibody according to the invention as a medicament. Advantageously, such a medicament is intended to treat the diseases in which FVIII inhibiting antibodies are produced.

Another object of the invention is the use of an antibody according to the invention for manufacturing a medicament.

In this respect, another object of the invention is the use of the antibody according to the invention for manufacturing a medicament used in the treatment of haemophilia A. For the purposes of the invention, the expression "used in the treatment of haemophilia A" must be understood as being equivalent to the expression "intended for the treatment of haemophilia A".

Advantageously, the treated haemophilia A is haemophilia A with inhibitors.

The anti-idiotypic antibody according to the invention can be administered to the patient at the same time as FVIII, either in the same medicament, or by two separate but concomitant administrations.

Finally, a last object of the invention relates to a pharmaceutical composition comprising an antibody according to the invention and one or more excipients and/or pharmaceutically acceptable vehicles. The excipient can be any solution, such as a saline, physiological, isotonic, buffered solution etc., as well as any suspension, gel, powder, etc., compatible with a pharmaceutical use and known to a person skilled in the art. The compositions according to the invention can moreover contain one or more agents or vehicles chosen from dispersants, solubilising agent, stabilizers, surfactants, preservatives, etc. On the other hand, the compositions according to the invention can comprise other agents or active ingredients.

Moreover, the compositions can be administered in different ways and in different forms. The administration can be carried out by any standard route for this type of therapeutic approach, such as in particular by systemic route, in particular by intravenous, intradermal, intratumoral, subcutaneous, intraperitoneal, intramuscular, intraarterial injection, etc.

There can for example be mentioned intratumoral injection or injection into an area close to the tumour or irrigating the tumour.

The doses can vary as a function of the number of administrations, the combination with other active ingredients, the stage of development of the pathology etc.

EXAMPLES

Example 1

Figure 1:
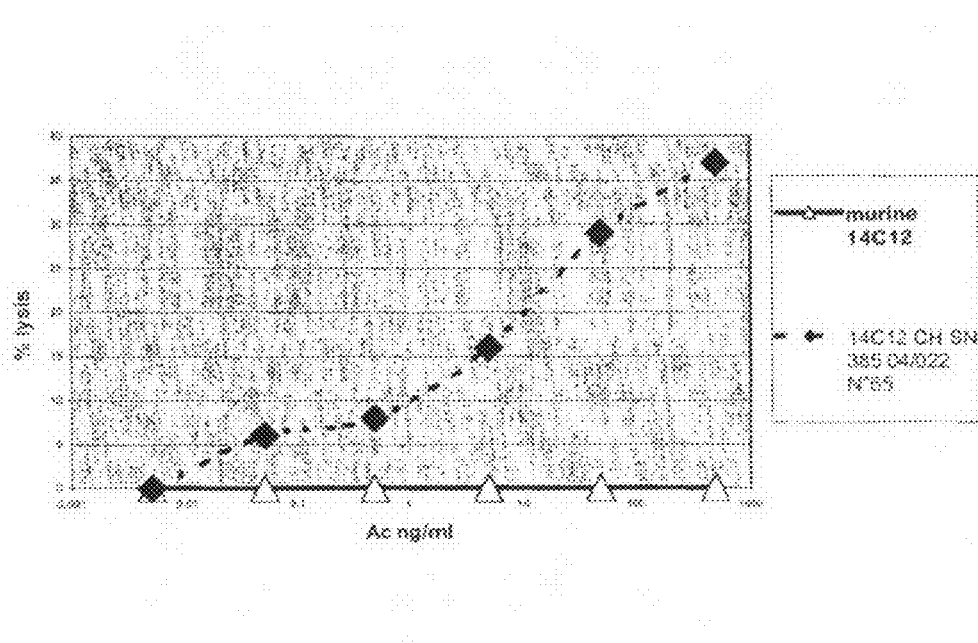
FIG. 1: Lysis of BO2C11 induced by the antibody EMAB565 (denoted 14C12 CH in the figure) in the presence of human NK cells.

Construction of the Expression Vectors of the Chimeric Antibody Anti-Id FVIII EMAB565

A. Determination of the Leader Sequence of the Variable Regions of the Murine Antibody 14C12

The total RNA of the murine hybridoma 14C12 producing an immunoglobulin of type IgG2a,κ was isolated. After reverse transcription, the variable domains of the light (Vκ) and heavy (VH) chains of the antibody 14C12 were amplified by the 5'RACE technique (Rapid Amplification of cDNA Ends) (GeneRacer kit, Invitrogen ref. L1500-01).

Briefly, a first reverse transcription stage was first carried out using a primer located in the 5' region of the murine constant regions Cκ or G1. A poly-dC sequence was then added to the 3' end of the synthesized cDNAs before carrying out the amplification of the Vκ and VH regions using a 5' primer recognizing the poly-dC sequence and a 3' primer, located in the murine constant regions Cκ or G1 at the 5' end of the reverse transcription primer. The primers used for these two stages are the following:

```
1. Reverse transcription primers
a. Murine kappa specific antisense primer
                                       (SEQ ID NO: 19)
5'- ACT GCC ATC AAT CTT CCA CTT GAC -3' b. Murine G2a specific antisense primer
                                       (SEQ ID NO: 20)
5'- CTG AGG GTG TAG AGG TCA GAC TG -3'

2. 5' RACE PCR primers
a. Murine kappa specific antisense primer
                                       (SEQ ID NO: 21)
5'- TTGTTCAAGAAGCACACGACTGAGGCAC -3' b. Murine G2a specific antisense primer
                                       (SEQ ID NO: 22)
5'- GAGTTCCAGGTCAAGGTCACTGGCTCAG -3'
```

The PCR products VH and Vκ thus obtained were cloned in the pCR4Blunt-TOPO vector (Zero blunt TOPO PCR cloning kit, Invitrogen, ref. K2875-20) then sequenced.

The nucleotide sequence of the Vκ region of the murine antibody 14C12 is indicated under the sequence SEQ ID NO: 1 and the deduced peptide sequence is the sequence SEQ ID NO: 9. The Vκ gene belongs to the sub-group Vκ23 [Almagro J C et al. Immunogenetics (1998), 47: 355-363]. The CDR1, CDR2 and CDR3 sequences of the Vκ region of the murine antibody 14C12, defined according to Kabat numbering [Kabat et al., "Sequences of Proteins of Immunological Interest", NIH Publication, 91-3242 (1991)], are indicated under the following sequences: SEQ ID NO: 13, SEQ ID NO: 14 and SEQ ID NO: 15, respectively. The CDR1-IMGT, CDR2-IMGT and CDR3-IMGT sequences of the Vκ region of the murine antibody 14C12, defined according to IMGT (international ImMunoGeneTics database) analysis [Lefranc, M.-P. et al., Dev. Comp. Immunol., 27, 55-77 (2003)] are indicated under the following sequences: SEQ ID NO: 27, SEQ ID NO: 28 and SEQ ID NO: 29, respectively. This definition, which differs from that of Kabat based solely on the analysis of sequence variability, takes into account and combines the characterization of the hypervariable loops [Chothia C. and Lesk A. M. J. Mol. Biol. 196: 901-17 (1987)] and the structural analysis of the antibodies by crystallography.

The nucleotide sequence of the VH region of 14C12 is the sequence SEQ ID NO: 2 and the deduced peptide sequence is the sequence SEQ ID NO: 10. The VH gene belongs to the VH1 sub-group [Honjo T. and Matsuda F. in "Immunoglobulin genes". Honjo T. and Alt F. W. eds, Academic Press, London (1996), pp 145-171]. The CDR1, CDR2 and CDR3 sequences of the VH region of the murine antibody 14C12, defined according to Kabat numbering [Kabat et al., "Sequences of Proteins of Immunological Interest", NIH Publication, 91-3242 (1991)], are indicated under the following sequences: SEQ ID NO: 16, SEQ ID NO: 17 and SEQ ID NO: 18, respectively. The CDR1-IMGT, CDR2-IMGT and CDR3-IMGT sequences of the VH region of the murine antibody 14C12, defined according to IMGT (international ImMunoGeneTics database) analysis [Lefranc, M.-P. et al., Dev. Comp. Immunol., 27, 55-77 (2003)] are indicated under the following sequences: SEQ ID NO: 30, SEQ ID NO: 31 and SEQ ID NO: 32, respectively. This definition, which differs from that of Kabat based solely on the analysis of sequence variability, takes into account and combines the characterization of the hypervariable loops [Chothia C. and Lesk A. M. J. Mol. Biol. 196: 901-17 (1987)] and the structural analysis of the antibodies by crystallography.

B. Construction of the Heavy Chain and Light Chain Expression Vectors of the Chimeric Antibody EMAB565

1. Kappa Light Chain Vector

The Vκ sequence cloned in the sequencing vector pCR4Blunt-TOPO was amplified using the following cloning primers:

```
a) VK sense primer:
                                       (SEQ ID NO: 23)
5'- GTATACTAGTGCCGCCACCATGGTTTTCACACCTCAGAT -3'
```

The underlined sequence corresponds to the restriction site Spe I, the sequence in bold type corresponds to a Kozak consensus sequence, the ATG initiator is in italics.

```
b) VK antisense primer
                                       (SEQ ID NO: 24)
5'- TGAAGACACTTGGTGCAGCCACAGTCCGTTTTATTTCCAACTTGG
TC -3'
```

This primer produces the joining of the murine Vκ sequences (in italics) and human constant region (Cκ) (in bold type). The underlined sequence corresponds to the Dra III restriction site.

The Vκ PCR product thus obtained contains the sequence coding for the natural peptide signal of the murine antibody 14C12. This Vκ PCR was then cloned between the Spe I and Dra III sites of the light chain chimerization vector at the 5' end of the human Cκ constant region, the nucleic sequence of which is the sequence SEQ ID NO: 4 and the deduced peptide sequence of which is the sequence SEQ ID NO 12. The human Cκ sequence of this chimerization vector was previously modified by silent mutagenesis in order to create a Dra III restriction site in order to allow the cloning of murine Vκ sequences. This chimerization vector contains a promoter well known to a person skilled in the art, such as CMV or RSV and a HGH (human Growth Hormone) polyadenylation sequence as well as the dhfr (dihydrofolate reductase) selection gene.

For the expression of the antibody EMAB565, the promoter of the chimerization vector was then replaced by the human EF-1 alpha promoter.

The light chain sequence of the chimeric antibody EMAB565 encoded by this vector is presented in SEQ ID NO: 5 for the nucleotide sequence and corresponds to the deduced peptide sequence SEQ ID NO: 7.

2. Heavy Chain Vector

A similar approach was used for the chimerization of the heavy chain of the antibody EMAB565. The VH sequence cloned in the pCR4Blunt-TOPO vector was first amplified using the following cloning primers:

a) VH sense primer
(SEQ ID NO: 25)
5'- CTATT<u>ACTAGT</u>GCCGCCACCATGGAATGGAGTTGGATATTT -3'

The underlined sequence corresponds to the Spe I restriction site, the sequence in bold type corresponds to a Kozak consensus sequence, the ATG initiator is in italics.

b) VH antisense primer
(SEQ ID NO: 26)
5'- GACCGAT<u>GGGCCC</u>TTGGTGGAGGCTGAGGAGACGGTGACCGTG -3'

This primer produces the joining of the murine VH sequences (in italics) and human G1 constant region (in bold type).

The underlined sequence corresponds to the Apa I restriction site.

The amplified VH fragment contains the sequence coding for the natural peptide signal of the murine antibody 14C12. This VH PCR was then cloned between the Spe I and Apa I sites of the heavy chain chimerization vector at the 5' end of the human γ1 constant region the nucleic sequence of which is the sequence SEQ ID NO: 3 and the deduced peptide sequence is the sequence SEQ ID NO: 11. This chimerization vector contains a promoter well known to a person skilled in the art, such as CMV or RSV and a bGH (bovine Growth Hormone) polyadenylation sequence as well as the neo selection gene.

For the expression of the antibody EMAB565, the promoter of the chimerization vector was then replaced by the human EF-1 alpha promoter.

The heavy chain sequence of the chimeric antibody EMAB565 encoded by this vector is presented in SEQ ID NO: 6 in the case of the nucleotide sequence and in sequence SEQ ID NO: 8 in the case of the deduced peptide sequence.

Example 2

Creation of a Cell Line Derived from the Line YB2/0 Producing the FVIII Anti-Inhibiting Chimeric Antibody EMAB565

The rat line YB2/0 (ATCC # CRL-1662) was cultured in EMS medium (Invitrogen, ref. 041-95181M) containing 5% foetal calf serum (FCS) (JRH Biosciences, ref. 12107). For the transfection, 5 million cells were electroporated (Biorad electroporator, model 1652077) in Optimix medium (Equibio, ref. EKITE 1) with 25 µg of Aat II linearized light chain vector, and 27 µg of Sca-I linearized heavy chain vector. The electroporation conditions applied were 230 volts and 960 microfarads per 0.5 ml cuvette. Each electroporation cuvette was then distributed over 5 96-well plates at a density of 5000 cells/well.

The introduction into RPMI selective medium (Invitrogen, ref 21875-034) containing 5% dialyzed serum (Invitrogen, ref. 10603-017), 500 µg/ml of geneticin G418 (Invitrogen, ref. 10131-027) and 25 nM of methotrexate (Sigma, ref. M8407), was carried out 3 days after the transfection.

The supernatants from the resistant transfection wells were screened for the presence of chimeric immunoglobulin (Ig) by ELISA assay specific to the human Ig sequences.

The 10 transfectants producing the most antibodies were amplified in 24-well plates and their supernatant re-assayed by ELISA in order to estimate their productivity and select the best 3 producers for cloning by limit dilution (40 cells/plate).

At the end of the cloning, the clone R565, hereafter called "R565", was selected for the production of the chimeric antibody EMAB565 and progressively adapted to the CD Hybridoma production medium (Invitrogen, ref. 11279-023).

The production of the chimeric antibody EMAB565 was carried out by expansion of the adapted culture in CD Hybridoma medium, obtained by dilution to $3 \times 10^5$ cells/ml in 75 cm$^2$ and 175 cm$^2$ flasks then by dilution to $4.5 \times 10^5$ cells/ml in roller type flasks. Having reached the maximum volume (1 l), the culture was continued until cell viability reached 20%. After production, the chimeric antibody EMAB565 was purified by protein A affinity chromatography (purity estimated by HPLC<95%) and checked by polyacrylamide gel electrophoresis.

The glycan analysis of the antibody composition produced (EMAB565) was carried out by HPCE-LIF and shows a fucose content of approximately 7%, a galactose content of approximately 52% and a fuc/Gal ratio equal to 0.133.

Example 3

Lysis of BO2C11 Induced by the Antibody EMAB565 in the Presence of Human NK Cells ADCC Technique The NK cells are isolated from the PBMCs (Peripheral Blood Mononuclear Cells) using the magnetic-activated cell separation (MACS) technique from Myltenyi. The NK cells are washed and resuspended in IMDM (Iscove's modified Dubelcco's Medium)+5% FCS ($45 \times 10^5$ cells/ml). The effector cells and the target cells are used in a ratio of 15/1. The target cells BO2C11 are adjusted to $3 \times 10^5$ cells/ml in IMDM+5% FCS. The antibodies are diluted in IMDM+0.5% FCS (final concentration 500; 50; 5; 0.5; 0.005 and 0.005 ng/ml).

The reaction mixture comprises 50 µl of antibodies, 50 µl of effector cells, 50 µl of target cells and 50 µl of IMDM medium in a 96-well microtitration plate. Two negative controls are set up:
- Lysis without NK: the NK effector cells are replaced by IMDM+5% FCS.
- Lysis without antibodies IAc): the antibodies are replaced by IMDM+5% FCS.

After incubation for 16 hours at 37° C. under an atmosphere enriched with 5% $CO_2$, the plates are centrifuged and the levels of intracellular LDH released into the supernatant evaluated by a specific reagent (Cytotoxicity Detection Kit 1 644 793).

The lysis percentage is estimated using a calibration range obtained with different dilutions of target cells lysed with Triton X100 (2%) corresponding to 100, 50, 25 and 0% lysis respectively.

The results are calculated according to the following formula:

%lysis=(%lysis with Antibodies and NK)−(%lysis without Antibodies)−(%lysis without NK).

The anti-idiotypic antibodies of murine 14C12 and chimeric EMABling 14C12 FVIII inhibitors studied for their ability to lyse the BO2C11 cells in the presence of NK cells.

FIG. 1 shows that the murine antibody 14C12 does not induce lysis of the BO2C11 cells since the chimeric antibody (EMABling Technology) induces a dose-dependent lysis.

Example 4

Secretion of IL-2 by Jurkat CD16 in the Presence of BO2C11 and of the Antibody EMAB565

This test estimates the ability of the antibodies to bind to the CD16 receptor (Fc gamma RIIIa) expressed on the Jurkat CD16 cells and to induce the secretion of IL2.

For this purpose, the following were mixed in 96-well plates:
- 50 µl of an antibody solution (final concentration at 25, 2.5, 0.25, 0.025, 0.012 µg/ml in IMDM with 5% FCS),
- 50 µl of PMA (dilution to 40 ng/ml in IMDM with 5% FCS), 50 µl of BO2C11 cells diluted to $6 \times 10^5$/ml in IMDM with 5% FCS, and 50 µl of Jurkat CD16 cells ($20 \times 10^6$/ml in IMDM with 5% FCS).

After incubation overnight at 37° C., the plates are centrifuged, and the IL2 contained in the supernatants evaluated with the commercial kit (Quantikine from R & D). The OD reading takes place at 450 nm.

The results are expressed in IL-2 levels as a function of the concentration of antibodies.

The anti-idiotypic antibody of the FVIII inhibitors EMAB565 is studied for its ability to induce the secretion of IL2 from Jurkat cells transfected with CD16 in the presence of BO2C11 cells.

Figure 2:
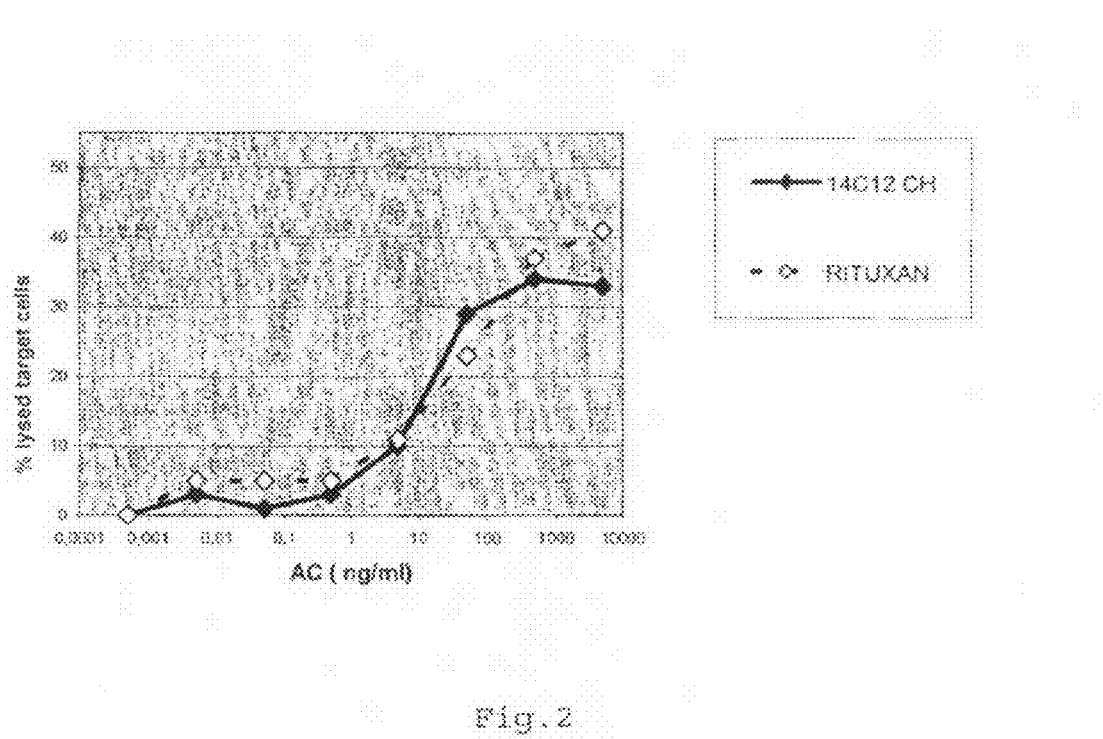
FIG. 2: Secretion of IL2 by Jurkat CD16 in the presence of BO2C11 and the antibody EMAB565 (denoted 14C12 CH in the figure).
Figure 3:
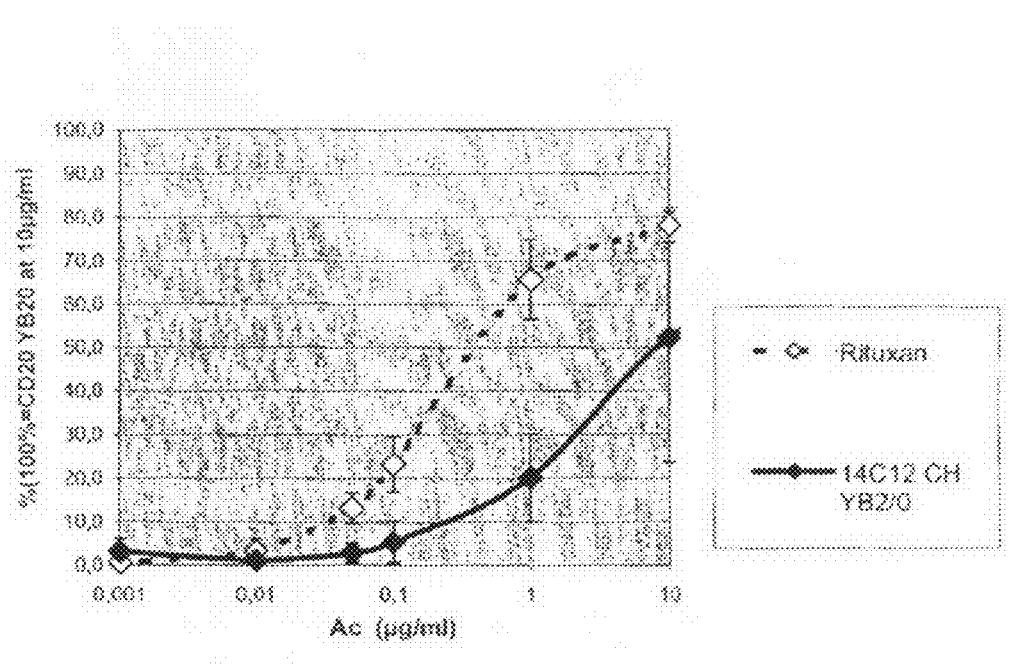
FIG. 3: Capping of the BCRs of BO2C11 induced by the antibody EMAB565 (denoted 14C12 CH in the figure).

FIG. 2 shows that the antibody EMAB565 induces the secretion of IL-2.

Example 5

Capping of the BCRs of BO2C11 Induced by the Antibody EMAB565

The BO2C11 cells ($1.2 \times 10^6$ cells/ml) are washed and preserved in IMDM containing 5% FCS, pH 7.4. The cells are incubated for 1 hour, 4 hours and 16 hours at 4° C. and 37° C. with the previously labelled antibody EMAB565 (ALEXA) at a concentration of 10 µg/ml. The capping of the receptors by the antibodies is visualized with a LEICA fluorescence microscope (×63 oil-immersion lens).

Figure 4:
FIG. 4: Apoptosis of BO2C11 induced by the antibody EMAB565 (denoted 14C12 CH in the figure).
Figure 4:
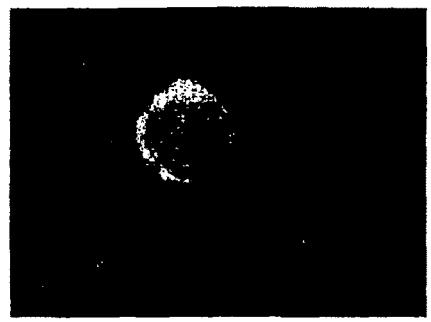

Different incubation times were studied and show that the capping intensity occurs early (30 minutes) and intensifies over time. By way of example, FIG. 4 shows that at 16 hours, the antibodies bound to BO2C11 are grouped at poles and not evenly distributed over the surface of the membrane. This indicates that the binding of the antibody 14C12 CH to BO2C11 induces a rearrangement of the membrane receptors and potentially the induction of a transduction signal.

Example 6

BO2C11 Apoptosis Induced by the Antibody EMAB565

The BO2C11 cells ($2.5 \times 10^5$) are incubated with the antibody EMAB565 (1 µg/ml) with or without crosslinker (goat F(ab2)' anti-human IgG Fcγ at 10 µg/ml) in 1 ml of RMPI with 10% FCS, in 24-well plates for 24 hours at 37° C. The cells are then centrifuged, washed twice in PBS, taken up in the buffer supplied with the kit and incubated with Annexin V-FITC and propidium iodide (PI) according to the recommendations of BD Biosciences. The cells are analyzed with a flow cytometer, the percentage of apoptotic cells corresponds to the cells labelled with annexin V (annexin V and annexin V+PI).

FIG. 4 shows that the induction of apoptosis in the presence of the antibody EMAB565 (EMABling technology) is less than 3% in the absence of cross linker and only 6.5% in the presence of cross-linker (FIG. 4).

Example 7

Lysis of BO2C11 Induced by the Antibody EMAB565 in the Presence of Complement

The BO2C11 cells are washed and incubated for 1 hour at 37° C. with different concentrations of the antibody EMAB565 (final concentration of 0 to 2.5 µg/ml) in the presence of a source of complement (Young rabbit complement from Cedarlane) diluted 1:10 in IMDM medium+FCS 5%. The cells are then centrifuged twice at 1200 rpm (270 g) for 1 minute and the supernatants are removed. The quantity of intracellular LDH released into the supernatant corresponding to cell lysis is measured by a specific reagent (Cytotoxicity Detection Kit 1 644 793).

The lysis percentage is estimated using a calibration range obtained with different dilutions of target cells lysed with Triton X-100 (2%) corresponding to 100, 50, 25 and 0% lysis respectively. The controls include spontaneous release (target cells only).

The results are calculated according to the following formula:

%lysis=(%lysis with Antibody and complement)− (%lysis without complement).

Figure 5:
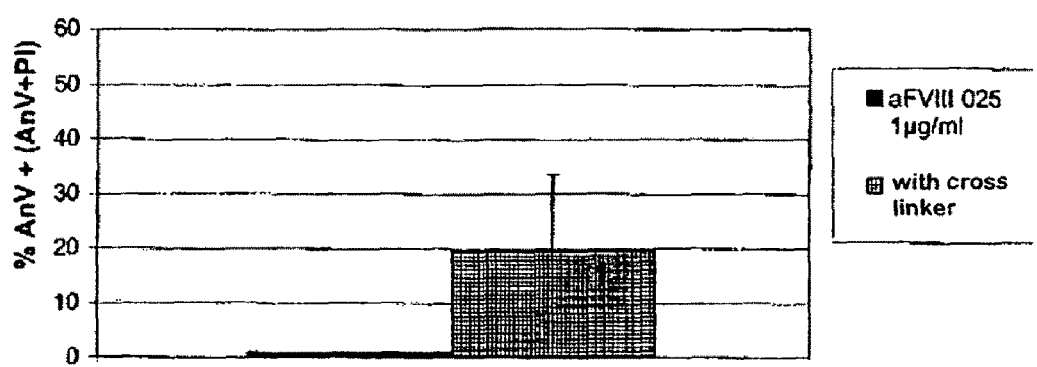
FIG. 5: Lysis of BO2C11 induced by the antibody EMAB565 (denoted 14C12 CH in the figure) in the presence of complement.

FIG. 5 shows that the CDC (Complement Dependant Cytotoxicity) activity induced by the antibody EMAB565 (EMABling technology) is 5% maximum in the case of the strongest antibody concentrations used.

The invention claimed is:

1. An anti-idiotypic monoclonal antibody directed against an antibody inhibiting human factor VIII (FVIII), said inhibiting antibody being directed against the C2 region of human FVIII, wherein the constant regions of said anti-idiotypic antibody's light chains and heavy chains are constant regions originating from a non-murine species, wherein each of said anti-idiotypic antibody's light chains is encoded by the murine-human chimeric nucleic acid sequence SEQ ID NO: 5 and wherein each of said anti-idiotypic antibody's heavy chains is encoded by the murine-human chimeric nucleic acid sequence SEQ ID NO: 6, and wherein the fucose level/galactose level ratio of the glycan structures of said anti-idiot is antibody, present on the glycosylation site of the Fc region, is less than or equal to 0.6.

2. An anti-idiotypic monoclonal antibody directed against an antibody inhibiting human factor VIII (FVIII), said inhibiting antibody being directed against the C2 region of human FVIII, wherein the variable region of each of said anti-idiotypic antibody's light chains is encoded by the murine nucleic acid sequence SEQ ID NO: 1, the variable region of each of said anti-idiotypic antibody's heavy chains is encoded by the murine nucleic acid sequence SEQ ID NO: 2, the constant regions of said anti-idiotypic antibody's light chains and heavy chains are constant regions originating from a non-murine species, wherein each of said anti-idiotypic antibody's light chains is encoded by the murine-human chimeric nucleic acid sequence SEQ ID NO: 5, wherein each of said anti-idiotypic antibody's heavy chains is encoded by the murine-human chimeric nucleic acid sequence SEQ ID NO: 6, wherein the peptide sequence of each of said anti-idiotypic antibody's light chains is the peptide sequence SEQ ID NO: 7 and wherein the peptide sequence of each of said anti-idiotypic antibody's heavy chains is the peptide sequence SEQ ID NO: 8, and wherein the fucose level/galactose level ratio of the glycan structures of said anti-idiotypic antibody, present on the glycosylation site of the Fc region, is less than or equal to 0.6.

3. The anti-idiotypic monoclonal antibody according to claim 1 or 2, characterized in that it is produced by a rat hybridoma cell line.

4. The anti-idiotypic monoclonal antibody according to claim 3, wherein the anti-idiotypic antibody is produced in the rat hybridoma YB2/0 (cell YB2/3HL.P2.G11.16Ag.20, deposited at the American Type Culture Collection under number ATCC CRL-1662).

5. The anti-idiotypic monoclonal antibody according to claim 3, wherein the anti-idiotypic antibody is capable of being produced by the clone R565 deposited under registration number 1-3510 in the Collection Nationale de Cultures de Microorganismes.

6. The anti-idiotypic monoclonal antibody according to claim 3, wherein the anti-idiotypic antibody is the antibody EMAB565 produced by the clone R565 deposited under registration number I-3510 in the Collection Nationale de Cultures de Microorganismes.

7. A stable cell line expressing an antibody according to claim 1 or 2.

8. An anti-idiotypic monoclonal antibody directed against an antibody inhibiting human factor VIII (FVIII), said inhibiting antibody being directed against the C2 region of human FVIII, wherein each of said anti-idiotypic antibody's light chains is encoded by the murine-human chimeric nucleic acid sequence SEQ ID NO: 5, and each of said anti-idiotypic antibody's heavy chains is encoded by the murine-human chimeric nucleic acid sequence SEQ ID NO: 6.

9. An anti-idiotypic monoclonal antibody directed against an antibody inhibiting human factor VIII (FVIII), said inhibiting antibody being directed against the C2 region of human FVIII, wherein the peptide sequence of each of the light chains of said anti-idiotypic antibody is the peptide sequence SEQ ID NO: 7 and the peptide sequence of each of the heavy chains of said anti-idiotypic antibody is the peptide sequence SEQ ID NO: 8.

10. An anti-idiotypic monoclonal antibody directed against an antibody inhibiting human factor VIII (FVIII), said inhibiting antibody being directed against the C2 region of human FVIII, wherein the constant regions of said anti-idiotypic antibody's light chains and heavy chains are constant regions originating from a non-murine species, wherein each of said anti-idiotypic antibody's light chains is encoded by the murine-human chimeric nucleic acid sequence SEQ ID NO: 5, and wherein each of said anti-idiotypic antibody's heavy chains is encoded by the murine-human chimeric nucleic acid sequence SEQ ID NO: 6.

11. An anti-idiotypic monoclonal antibody directed against an antibody inhibiting human factor VIII (FVIII), said inhibiting antibody being directed against the C2 region of human FVIII, wherein the constant regions of said anti-idiotypic antibody's light chains and heavy chains are constant regions originating from a non-murine species, wherein each of said anti-idiotypic antibody's light chains is encoded by the murine-human chimeric nucleic acid sequence SEQ ID NO: 5, wherein each of said anti-idiotypic antibody's heavy chains is encoded by the murine-human chimeric nucleic acid sequence SEQ ID NO: 6, wherein the peptide sequence of each of said anti-idiotypic antibody's light chains is the peptide sequence SEQ ID NO: 7, and wherein the peptide sequence of each of said anti-idiotypic antibody's heavy chains is the peptide sequence SEQ ID NO: 8.

* * * * *